(12) United States Patent
Tano et al.

(10) Patent No.: US 7,403,822 B2
(45) Date of Patent: Jul. 22, 2008

(54) VISUAL RESTORATION AIDING DEVICE

(75) Inventors: Yasuo Tano, Kobe (JP); Takashi Fujikado, Toyonaka (JP)

(73) Assignee: Nidek Co., Ltd., Gamagori (JP)

( * ) Notice: Subject to any disclaimer, the term of this patent is extended or adjusted under 35 U.S.C. 154(b) by 141 days.

(21) Appl. No.: 11/184,911

(22) Filed: Jul. 20, 2005

(65) Prior Publication Data

US 2006/0074461 A1 Apr. 6, 2006

(30) Foreign Application Priority Data

Jul. 23, 2004 (JP) ............................. 2004-215943

(51) Int. Cl.
*A61N 1/00* (2006.01)
(52) U.S. Cl. ...................................... 607/53
(58) Field of Classification Search .................. 607/53, 607/54; 623/6.63, 4.1
See application file for complete search history.

(56) References Cited

U.S. PATENT DOCUMENTS

| | | | |
|---|---|---|---|
| 5,016,633 A | | 5/1991 | Chow |
| 5,109,844 A | | 5/1992 | de Juan, Jr. et al. |
| 5,865,839 A | * | 2/1999 | Doorish ...................... 623/6.63 |
| 5,895,415 A | * | 4/1999 | Chow et al. .................... 607/54 |
| 5,935,155 A | * | 8/1999 | Humayun et al. ............. 607/54 |
| 6,230,057 B1 | * | 5/2001 | Chow et al. .................... 607/54 |
| 6,347,250 B1 | | 2/2002 | Nisch et al. |
| 6,389,317 B1 | * | 5/2002 | Chow et al. .................... 607/54 |
| 7,113,828 B2 | * | 9/2006 | Yagi et al. ...................... 607/54 |
| 2002/0010496 A1 | * | 1/2002 | Greenberg et al. ............. 607/54 |
| 2002/0038134 A1 | * | 3/2002 | Greenberg et al. ............. 607/1 |
| 2002/0091422 A1 | * | 7/2002 | Greenberg et al. ............. 607/54 |
| 2002/0188282 A1 | | 12/2002 | Greenberg |
| 2003/0181957 A1 | | 9/2003 | Greenberg et al. |
| 2004/0102843 A1 | | 5/2004 | Yagi |
| 2004/0116980 A1 | | 6/2004 | Ohta et al. |
| 2004/0193232 A1 | * | 9/2004 | Yagi et al. ...................... 607/54 |

FOREIGN PATENT DOCUMENTS

| | | |
|---|---|---|
| JP | A-2004-298298 | 10/2007 |
| WO | WO 94/26209 | 11/1994 |
| WO | WO 96/39221 | 12/1996 |

(Continued)

*Primary Examiner*—Carl H. Layno
*Assistant Examiner*—Jon-Eric C. Morales
(74) *Attorney, Agent, or Firm*—Oliff & Berridge, PLC

(57) ABSTRACT

A visual restoration aiding device for restoring vision of a patient, comprises: a substrate which will be placed on or under a retina, a choroid or a sclera of a patient's eye; a plurality of electrodes arranged on the substrate for applying electrical stimulation pulse signals to cells constituting the retina; a photographing unit which photographs an object to be recognized by the patient; and a control unit which controls output of the electrical stimulation pulse signals from each electrode based image data captured by the photographing unit. The number of the electrodes placed on the substrate is less than the number of electrodes that can simultaneously output the electrical stimulation pulse signals based on the image data corresponding to one frame. The control unit is configured to sequentially output the electrical stimulation pulse signals at predetermined time interval based on the divided image data corresponding to one frame so as to allow the patient to recognize the image corresponding to one frame by joining two or more divided sections of the image corresponding to one frame.

5 Claims, 5 Drawing Sheets

FOREIGN PATENT DOCUMENTS

| | | |
|---|---|---|
| WO | WO 99/45870 | 9/1999 |
| WO | WO 00/56393 | 9/2000 |
| WO | WO 01/74444 A1 | 10/2001 |
| WO | WO 02/40095 A1 | 5/2002 |
| WO | WO 02/064072 A1 | 8/2002 |
| WO | WO 02/080828 A1 | 10/2002 |
| WO | WO 02/089912 A2 | 11/2002 |

* cited by examiner

PATIENT'S EYE

VISUAL RESTORATION AIDING DEVICE

BACKGROUND OF THE INVENTION

1. Field of the Invention

The present invention relates to a visual restoration aiding device for inducing restoration of vision.

2. Description of Related Art

There have been proposed a visual restoration aiding device for inducing restoration of vision by applying electrical stimulation to cells constituting a retina from electrodes placed (implanted) in an eye (see U.S. Pat. No. 5,109,844, U.S. Pat. No. 5,935,155). In the case where such device is used for allowing a patient to have a wide visual field and recognize an object with a good resolution, it is necessary to place many electrodes on the retina, a choroid or a sclera. However, in view of device design or operative method, and further load on a patient, there is a limit to the number of electrodes allowed to be placed. It is desired that the number of electrodes is as small as possible.

SUMMARY OF THE INVENTION

The present invention has been made in view of the above circumstances and has an object to overcome the above problems and to provide a visual restoration aiding device which allows a patient to recognize an object with a limited number of electrodes and is effective for downsizing the device and facilitating a manually placing work.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a visual restoration aiding device for restoring vision of a patient, comprising: a substrate which will be placed on a retina, a choroid or a sclera of a patient's eye; a plurality of electrodes arranged on the substrate for applying electrical stimulation pulse signals to cells constituting the retina; a photographing unit which photographs an object to be recognized by the patient; and a control unit which controls output of the electrical stimulation pulse signals from each electrode based image data captured by the photographing unit; wherein the number of the electrodes arranged on the substrate is less than the number of electrodes needed for simultaneously outputting the electrical stimulation pulse signals based on the image data corresponding to one frame, and the control unit is configured to sequentially output the electrical stimulation pulse signals at predetermined time interval based on the divided image data corresponding to one frame so as to allow the patient to recognize the image corresponding to one frame by joining two or more divided sections of the image corresponding to one frame.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
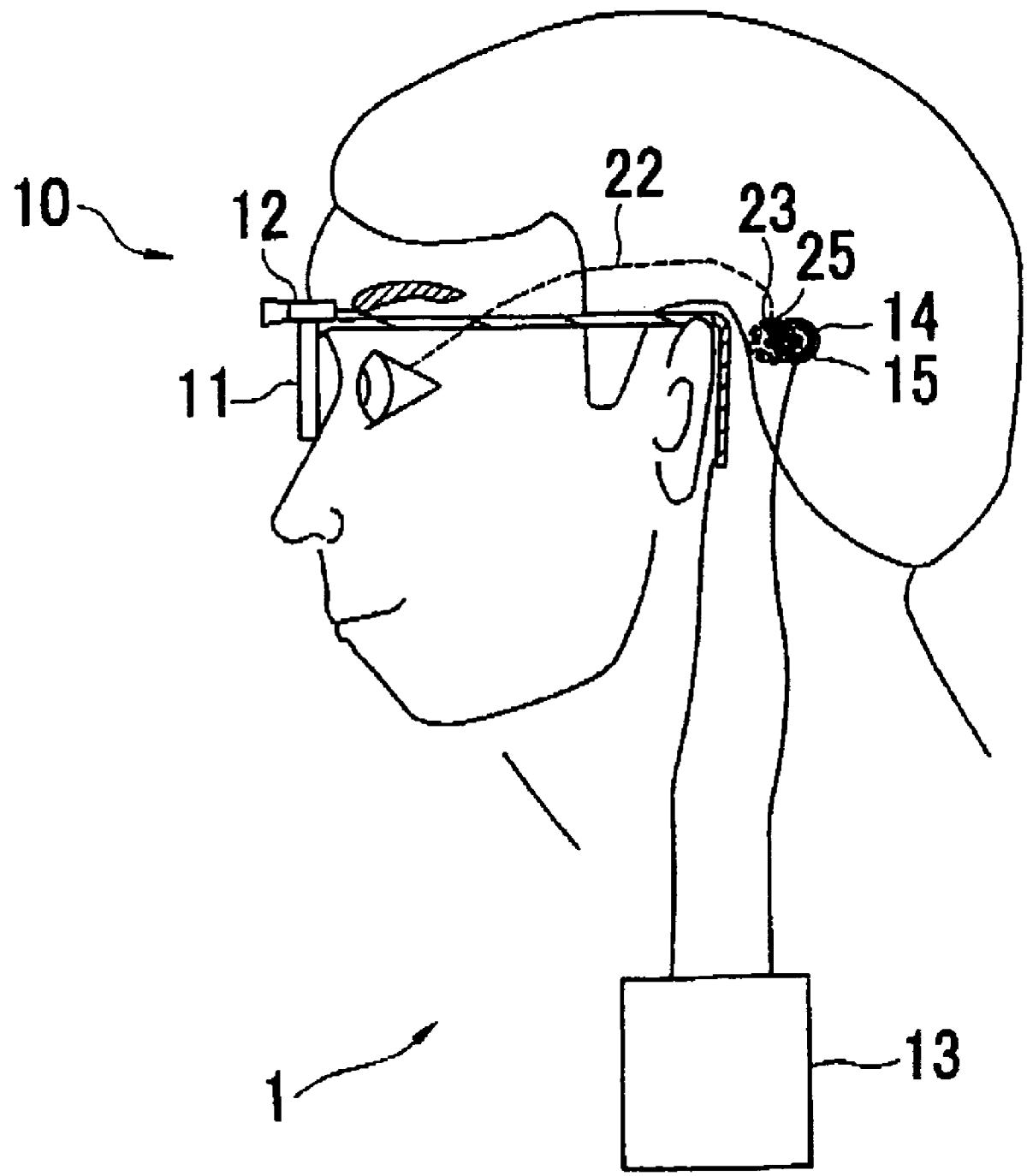
FIG. 1 is a schematic structural view of a visual restoration aiding device in a present embodiment.
Figure 2A:
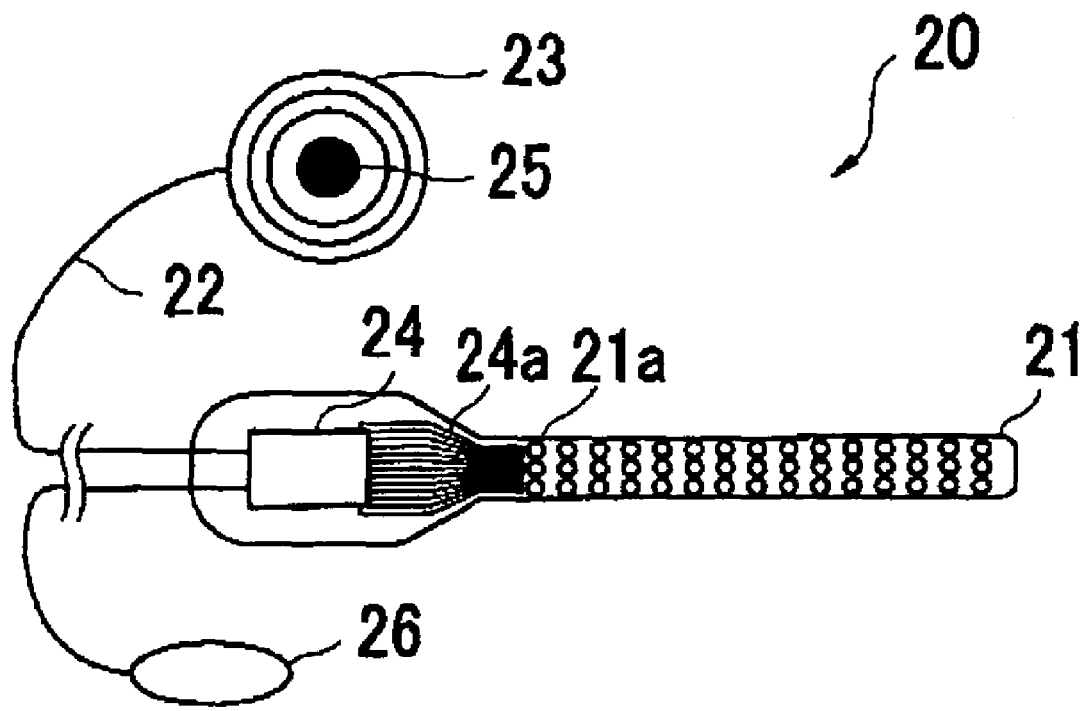
FIG. 2 is a schematic structural view of an internal device.
Figure 2B:
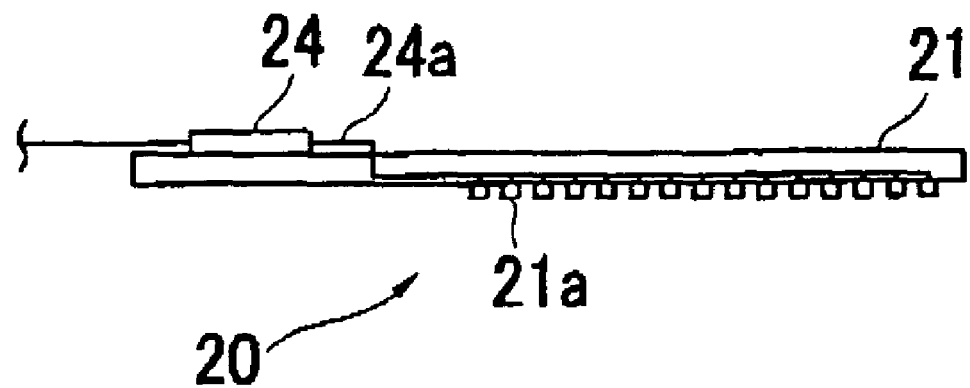
Figure 3:
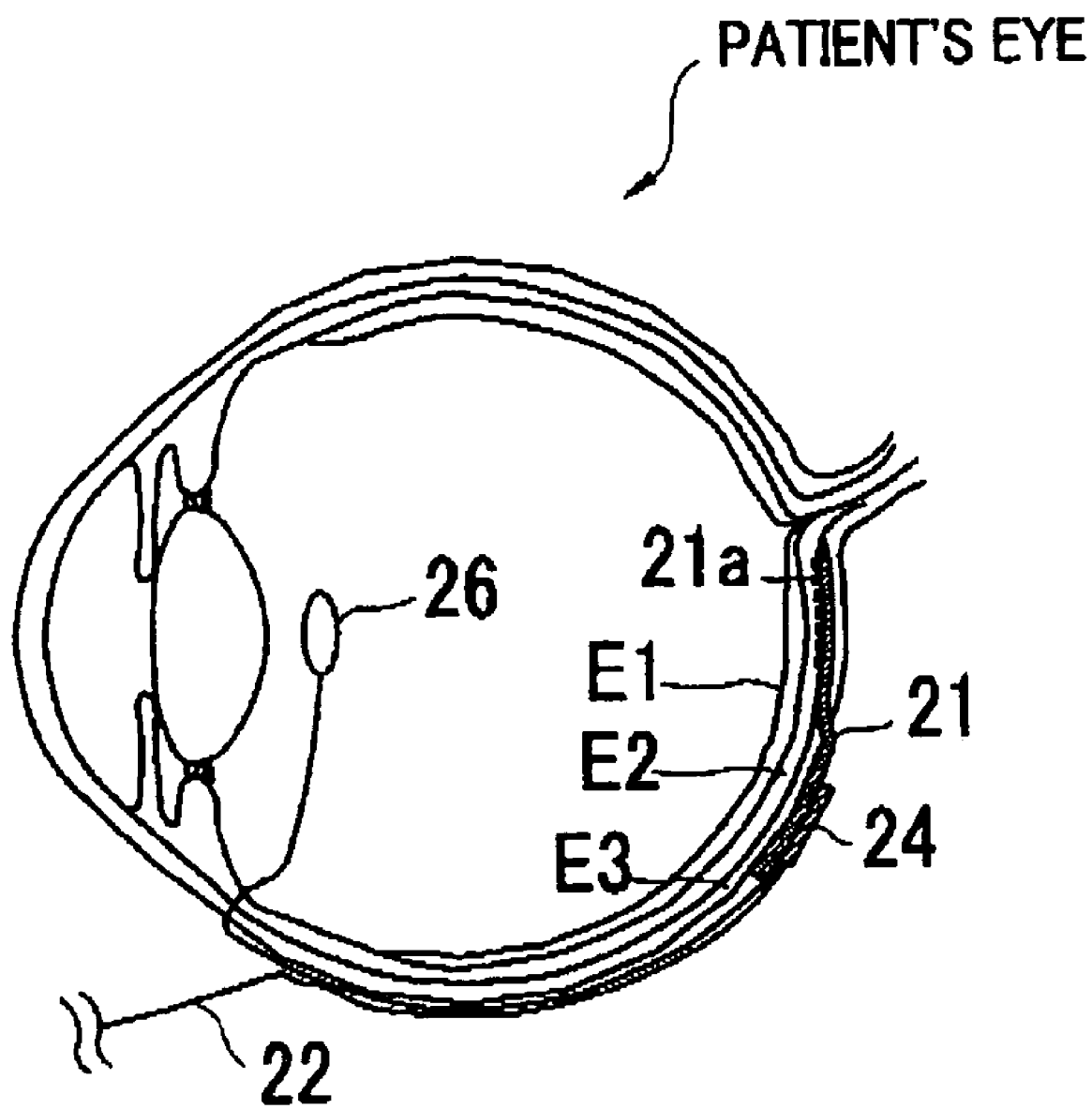
FIG. 3 is a view showing the internal device placed in an eye.
Figure 4:
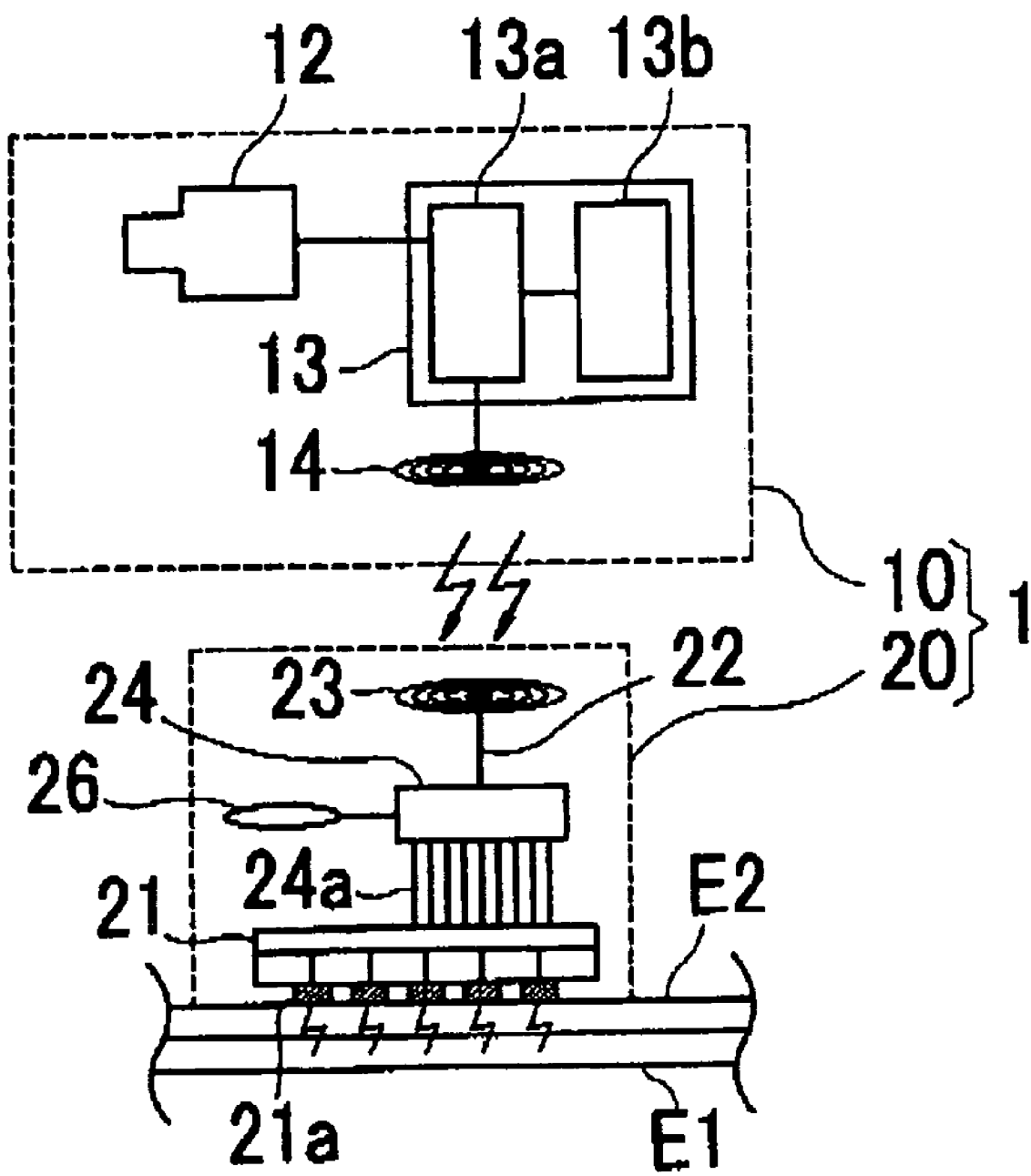
FIG. 4 is a block diagram showing a control system of the visual restoration aiding device.

A detailed description of a preferred embodiment of the present invention will now be given referring to the accompanying drawings. FIG. 1 is a schematic structural view of a visual restoration aiding device in the present embodiment. FIG. 2 is a schematic structural view of an internal device of the visual restoration aiding device. FIG. 3 is a view showing a state where the internal device is placed in an eye. FIG. 4 is a schematic block diagram of a control system of the device.

A visual restoration aiding device 1 mainly includes an external device 10 which photographs the external world, or captures surrounding images, and an internal device 20 which applies electrical stimulation to the cells constituting a retina to induce the restoration of vision. The external device 10 includes a visor 11 which a patient will put on, a photographing unit 12 such as a CCD camera mounted on the visor 11, an external unit 13, and a transmitting unit 14 including a primary coil. The visor 11 is shaped like eyeglasses, which is put on the front of a patient's eye during use. The photographing unit 12 is mounted on the front of the visor 11 and photographs an object to be recognized by the patient.

The external unit 13 includes a signal converting unit 13a having a processing circuit such as a CPU and a power supply unit 13b for power supply to the device 1 (i.e., the external device 10 and the internal device 20). The signal converting unit 13a makes an image processing on image data captured by the photographing unit 12 and further converts image-processed data to data for electrical stimulation pulse signal. The transmitting unit 14 transmits the data for electrical stimulation pulse signal converted by the signal converting unit 13a and electric power in the form of electromagnetic waves to the internal device 20. The transmitting unit 14 is centrally provided with a magnet 15. This magnet 16 is used to enhance a data transmitting efficiency of the transmitting unit 14 and to fix the transmitting unit 14 in place relative to a receiving unit 23 which will be mentioned later.

The internal device 20 includes a substrate 21 on which a plurality of electrodes 21a are placed (arranged), a cable 22, the receiving unit 23 including a secondary coil, an internal unit 24 placed on the substrate 21, and an indifferent electrode 26.

The substrate 21 is made of a material with good biocompatibility and foldable in a predetermined thickness, such as polypropylene and polyimide. The substrate 21 is formed from a substantially rectangular thin plate having a thickness of about 10 µm to about 100 µm, a length of about 10 mm to about 30 mm in a long side and a length of about 1 mm to about 5 mm in a short side.

The electrodes 21a are arranged two or more at equal intervals in each of the long side and the short side of the substrate 21. Thus, an electrode array is formed. In the present embodiment, the electrodes 21a are arranged fifteen in the long side of the substrate 21 and three in the short side.

In the present embodiment, the electrode array constituted of the electrodes 21a is placed on a sclera E3 (between a choroid E2 and the sclera E3) to electrically stimulate the cells constituting a retina E1, but it is not limited thereto. For instance, the electrode array may be set on the choroid E2 (between the retina E1 and the choroid E2) or on the retina E1.

The receiving unit 23 receives the data for electrical stimulation pulse signal and data for electric power transmitted from the external device 10. The receiving unit 23 is centrally provided with a magnet 25. The transmitting unit 14 and the receiving unit 23 in the present embodiment are placed on a temporal region of the patient, but not limited thereto. It is essential only that these units can transmit the data for electrical stimulation pulse signal and the data for electric power from outside to inside the body. For example, the transmitting unit 14 is attached on the front of the patients eye and the receiving unit 23 is placed in the patient's eye (e.g., near an anterior segment) to face the transmitting unit 14.

The internal unit 24 is constituted of an IC including a circuit which divides the signals received by the receiving unit 23 into the data for electrical stimulation pulse signal and the data for electric power, a circuit which converts the data for electrical stimulation pulse signal into electrical stimulation pulse signals, a circuit which transmits the electrical stimulation pulse signals to each electrode 21a, and others. With such structure, the internal unit 24 processes the data for electrical stimulation pulse signal and then outputs the converted electrical stimulation pulse signals from each electrode 21a. It is to be noted that the electrodes 21a are connected individually to the internal unit 24 through a plurality of lead wires 24a formed on the substrate 21. The internal unit 24 obtains electric power for driving the internal device 20 from the data for electric power received by the receiving unit 23.

The indifferent electrode 26 is connected to the internal unit 24 and placed so that a tip portion extends into the eye after passing along the outside of an eyeball and penetrating the pars plana of ciliary body so that the tip portion faces the substrate 21, interposing the retina E1 and the choroid E2. The tip portion of the indifferent electrode 26 is of a ring shape in order to efficiently function as the indifferent electrode. However, other shapes may be adopted. For example, it may be of even a simple linear shape. The indifferent electrode 26 in the present embodiment is placed in the eye after penetrating the pars plana of ciliary body, but it is not limited thereto. The indifferent electrode 26 may be placed anywhere only if it can efficiently apply the electrical stimulation pulse signals output from the electrodes 21a to the cells of the retina. For instance, the indifferent electrode 26 may be disposed in an adjacent area of the electrodes 21a. A further alternative is to provide no indifferent electrode 26.

With the visual restoration aiding device 1 having the above structure, the output control of the electrical stimulation pulse signals for restoration of vision is explained below.

Image data captured by the photographing unit 12 is input to the signal converting unit 13a. This input image data is converted by the signal converting unit 13a into a signal (the data for electrical stimulation pulse signal) of a predetermined band and is transmitted to the internal device 20 through the transmitting unit 14.

The electric power supplied from the power supply unit 13b is converted by the signal converting unit 13a into a signal of a band different from the data for electrical stimulation pulse signal and is transmitted to the internal device 20 in combination with the data for electrical stimulation pulse signal.

The receiving unit 23 receives the data for electrical stimulation pulse signal and the data for electric power, both being transmitted from the external device 10, and inputs them to the internal unit 24. The internal unit 24 extracts the input data for electrical stimulation pulse signal, forms electrical stimulation pulse signals based on the extracted data, and outputs the electrical stimulation pulse signals from each electrode 21a. The unit 24 also obtains electric power for driving the internal device 20 from the input data for electric power.

FIGS. 5A to 5E are views to explain a method using the electrode array in the present embodiment for allowing the patient to recognize an image corresponding to one frame captured by the photographing unit 12. Each square box in FIGS. 5A to 5E indicates each electrode 21a of the electrode array. Each hatched box of the square boxes represents the electrode 21a from which electrical stimulation pulse signals are output. An object to be recognized by the patient is a triangular object having such a size that the entire object cannot be recognized at a time (simultaneously) with the electrode array in the present embodiment.

Figure 5A:
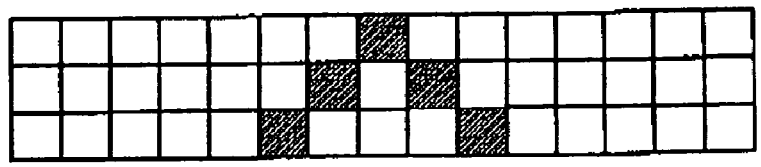
FIGS. 5A to 5E are views to explain output of electrical stimulation pulse signals based on image data corresponding to one frame in a scrolling mode.
Figure 5B:
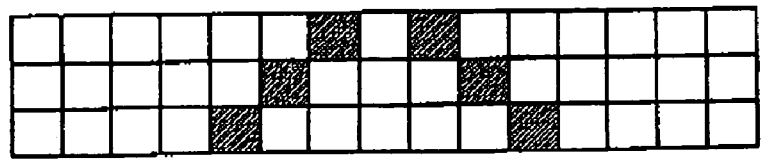
Figure 5C:
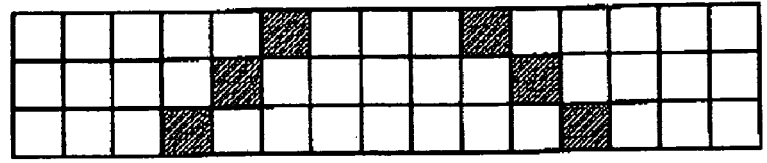
Figure 5D:
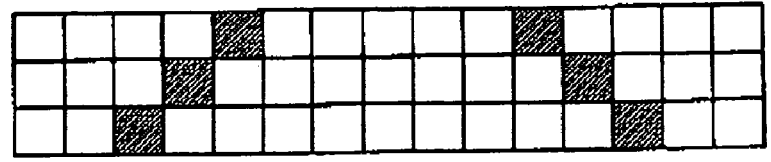
Figure 5E:
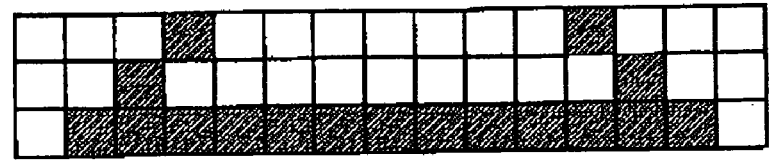

The internal unit 24 first outputs the electrical stimulation pulse signals from the electrodes 21a for allowing the patient to recognize an apex portion of the triangular object (see FIG. 5A). Secondly, the internal unit 24 sequentially outputs the electrical stimulation pulse signals from the electrodes 21a for allowing the patient to sequentially recognize the triangular object from an apex side to a bottom side (see FIGS. 5B to 5E). Consequently, the patient is able to entirely recognize the triangular object. In the present embodiment, the object is allowed to recognize from the apex side to the bottom side, but it is not limited thereto. For instance, the patient may recognize the object from the bottom side to the apex side, a left side to a right side, or the right side to the left side. That is, any direction may be adopted for allowing the patient to recognize the object.

The case for recognition of the object of a simple form is explained as above. Besides, the same output control can be applied to an object of a complicated shape to allow the patient to recognize the entire object. In this case, the signal converting unit 13a conducts image processing for extracting the features of the object or simplifying the object in order to make the shape of the object easy to recognize, and then the internal unit 24 performs the output control of the electrical stimulation pulse signals from the electrode array.

In the above embodiment, the electrical stimulation pulse signals based on the image data corresponding to one frame are output from the electrode array in the scrolling mode. However, it is not limited to this. As an alternative, the electrical stimulation pulse signals based on the image data corresponding to one frame may be output sequentially at predetermined time intervals so that the patient may recognize the image corresponding to one frame by joining two or more divided sections of the image corresponding to the one frame.

Figure 6:
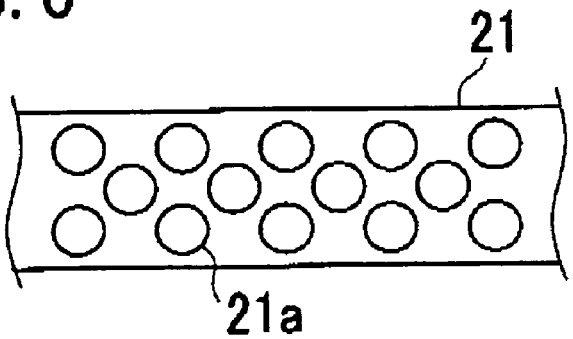
FIG. 6 is a view showing electrodes arranged in a honeycomb pattern on a substrate.

Further, the arrangement of the electrodes 21a is 15×3 in the present embodiment. Another arrangement may be adopted if only the electrodes 21a can be set on the substrate having such a size that it can be placed in the eye and also the number of electrodes 21a necessary for the above mentioned output control of the electrical stimulation pulse signals can be ensured. Further, the arrangement of electrodes 21a may be a honeycomb pattern (see FIG. 6).

As above, according to the device of the present invention, in which a certain number of electrodes is used regardless of the size of an object, it is possible to facilitate device design and manufacture. The number of electrodes needed for simultaneously allowing recognition of the entire object can be reduced and the area of the substrate can be decreased. This makes it possible to easily bring the entire surface of the substrate in contact with the curved surface of the retina. Consequently, irregular contact between the electrodes and the portions to be stimulated can be prevented and thus uneven charge injection amounts of each electrode can be reduced. The area of the substrate can be decreased, which facilitates placing of the device in the eye.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A visual restoration aiding device for restoring vision of a patient, comprising:
   a substrate which will be placed on a retina, a choroid or a sclera of a patient's eye;
   an electrode array including a plurality of electrodes arranged on the substrate for applying electrical stimulation pulse signals to cells constituting the retina;
   a photographing unit which photographs an object to be recognized by the patient; and
   a control unit which controls output of the electrical stimulation pulse signals from each electrode of the electrode array based on image data captured by the photographing unit;
   wherein the control unit is configured to divide the image data corresponding to one frame captured by the photographing unit into a plurality of partial data in one of a vertical direction and a horizontal direction of the image data, to form the electrical stimulation pulse signals corresponding to each of the plurality of divided partial data, and to switch and output the formed electrical stimulation pulse signals from the electrode array at predetermined time intervals in the order along the direction of division of the image data corresponding to one frame so as to allow the patient to recognize the image corresponding to one frame.

2. The visual restoration aiding device according to claim 1, wherein the control unit outputs the formed electrical stimulation pulse signals in a scrolling mode.

3. The visual restoration aiding device according to claim I, wherein the substrate has a narrow elongated shape, and
   the electrodes are arranged two or more in a long side and a short side of the substrate respectively.

4. The visual restoration aiding device according to claim 3, wherein the substrate is of a length of about 10 mm to about 30 mm in the long side and a length of about 1 mm to about 5 mm in the short side.

5. The visual restoration aiding device according to claim 3, wherein the electrodes are arranged in a honeycomb pattern on the substrate.

* * * * *